(12) United States Patent
Birkeland

(10) Patent No.: US 9,474,808 B2
(45) Date of Patent: Oct. 25, 2016

(54) DESALINATION OF A COMPOSITION COMPRISING A CONTRAST AGENT

(75) Inventor: Aslaug Birkeland, Lindesnes (NO)

(73) Assignee: GE HEALTHCARE AS, Oslo (NO)

( * ) Notice: Subject to any disclaimer, the term of this patent is extended or adjusted under 35 U.S.C. 154(b) by 0 days.

(21) Appl. No.: 13/995,588

(22) PCT Filed: Dec. 20, 2011

(86) PCT No.: PCT/EP2011/073377
§ 371 (c)(1),
(2), (4) Date: Jun. 19, 2013

(87) PCT Pub. No.: WO2012/084926
PCT Pub. Date: Jun. 28, 2012

(65) Prior Publication Data
US 2013/0277221 A1    Oct. 24, 2013

(30) Foreign Application Priority Data
Dec. 21, 2010 (EP) .................................. 10196117

(51) Int. Cl.
| A61K 49/04 | (2006.01) |
| A61K 49/06 | (2006.01) |
| C07C 231/24 | (2006.01) |
| C07C 237/46 | (2006.01) |
| B01D 61/44 | (2006.01) |
| A61K 49/00 | (2006.01) |
| B01D 61/42 | (2006.01) |
| B01D 61/58 | (2006.01) |
| C02F 1/469 | (2006.01) |

(52) U.S. Cl.
CPC ....... *A61K 49/0002* (2013.01); *A61K 49/0438* (2013.01); *A61K 49/0442* (2013.01); *B01D 61/422* (2013.01); *B01D 61/44* (2013.01); *B01D 61/58* (2013.01); *C02F 1/4695* (2013.01); *C07C 231/24* (2013.01)

(58) Field of Classification Search
CPC .. A61K 49/04; A61K 49/0002; A61K 49/06; C07C 231/24; C07C 237/46
See application file for complete search history.

(56) References Cited

U.S. PATENT DOCUMENTS

| 5,204,086 | A | * | 4/1993 | Wille .......................... 424/9.454 |
| 5,210,300 | A | * | 5/1993 | Kneller ......................... 564/153 |
| 5,254,227 | A | | 10/1993 | Cawfield et al. |
| 5,811,581 | A | * | 9/1998 | Piva et al. .................... 564/153 |
| 6,495,014 | B1 | * | 12/2002 | Datta et al. ................... 204/533 |
| 8,163,965 | B2 | * | 4/2012 | Cervenka et al. ............ 570/211 |
| 2006/0027457 | A1 | * | 2/2006 | Sato .............................. 204/524 |
| 2006/0178533 | A1 | * | 8/2006 | Holmaas et al. ............. 564/152 |
| 2009/0048463 | A1 | * | 2/2009 | Galindro et al. ............. 564/153 |
| 2011/0021823 | A1 | * | 1/2011 | Homestad et al. ........... 564/153 |
| 2011/0180477 | A1 | * | 7/2011 | Ganzi et al. .................. 210/638 |
| 2012/0283474 | A1 | * | 11/2012 | Hu et al. ....................... 564/153 |

FOREIGN PATENT DOCUMENTS

| CA | 2280535 | 2/2000 |
| WO | 97/30735 | 8/1997 |

OTHER PUBLICATIONS

PCT/EP2011/073377 ISRWO Dated May 22, 2012.

* cited by examiner

*Primary Examiner* — Keith Hendricks
*Assistant Examiner* — Salil Jain
(74) *Attorney, Agent, or Firm* — Wood IP LLC

(57) ABSTRACT

The invention relates to industrial preparation of contrast agents, and further to an improved process for the purification of contrast agents. In particular, it relates to a process for reducing the salt content of compositions comprising an MR contrast agent or an X-ray contrast agent, such as a non-ionic iodinated monomeric compound or a non-ionic iodinated dimeric compound.

17 Claims, No Drawings

DESALINATION OF A COMPOSITION COMPRISING A CONTRAST AGENT

This invention relates generally to industrial preparation of contrast agents, and further to an improved process for the purification of contrast agents. In particular, it relates to a process for reducing the salt content of compositions comprising an X-ray contrast agent or an MR contrast agent.

In techniques such as X-ray, one approach to improve the diagnostic quality factor has been to introduce contrast enhancing materials formulated as contrast media into the body region being imaged. Thus for X-ray, early examples of contrast agents were insoluble inorganic barium salts which enhanced X-ray attenuation in the body zones into which they distributed. For the last 50 years the field of X-ray contrast agents has been dominated by soluble iodine containing compounds. Commercial available contrast media containing iodinated contrast agents are usually classified as ionic monomers such as diatrizoate (marketed e.g. under the trade mark Gastrografen™), ionic dimers such as ioxaglate (marketed e.g. under the trade mark Hexabrix™), nonionic monomers such as iohexol (marketed e.g. under the trade mark Omnipaque™), iopamidol (marketed e.g. under the trade mark Isovue™), iomeprol (marketed e.g. under the trade mark Iomeron™) and the non-ionic dimer iodixanol (marketed under the trade mark Visipaque™). The clinical safety of iodinated X-ray contrast media has continuously been improved over the recent decades through development of new agents; from ionic monomers (Isopaque™) to non-ionic monomers (e.g. Omnipaque™) and non-ionic dimers (e.g. Visipaque™).

The manufacture of non-ionic X-ray contrast media involves the production of the chemical drug, the contrast agent (referred to as the primary production), followed by the formulation into the drug product (referred to as the secondary production). In the preparation of an X-ray composition, i.e. the secondary production of a contrast media, the contrast agent is admixed with additives, such as salts, optionally after dispersion in a physiologically tolerable carrier. Primary production of the contrast agent normally involves a multi step chemical synthesis and a thorough purification process. For a commercial drug product, it is important for the primary production to be efficient and economical and to provide a drug substance fulfilling the regulatory specifications, such as those mandated by US Pharmacopeia. In addition, the cost and efficiency of the secondary production depend on the synthesis and purification processes in the primary production. It is therefore critical to optimize each process in the primary production of the contrast agent.

Iohexol is the non-proprietary name of the non-ionic iodinated X-ray contrast agent of the chemical drug substance 5-[N-(2,3-dihydroxypropyl)-acetamido]-N,N'-bis(2,3-dihydroxypeopyl)-2,4,6-triiodoisophtalamide. The drug product is marketed under the trade name Omnipaque®. The manufacture of iohexol involves the production of the chemical drug substance (primary production) followed by formulation into the drug product (secondary production).

The final synthesis step of iohexol primary production is an N-alkylation step in which 5-acetamido-N,N'-bis(2,3-dihydroxypropyl)-2,4,6-triiodoisophthalamide (Compound A) is reacted with an alkylating agent to introduce the 2,3-dihydroxypropyl group at the nitrogen of the 5-acetamido group. The reaction mixture, or crude composition, after this alkylation step, includes a considerable amount of salts, mainly in the form of sodium chloride (NaCl). Hence, the prepared crude composition comprising the X-ray contrast agent iohexol includes considerably amounts of salts. The sources of chloride are 1-chloro-2,3-propanediol, used as the alkylating agent, and hydrochloric acid, which is used to adjust the pH. The source of sodium cations is the sodium hydroxide (NaOH). After the final reaction step of the primary production process, iohexol has to be purified by desalinating the composition, before crystallization. In order to crystallize iohexol in accordance with the regulatory purity requirement, the salt content prior to a crystallization process should be less than about 0.02 w/w % relative to iohexol. Further, after the crystallization step, the composition is subjected to further purification to obtain a composition comprising iohexol with a salt content below about 0.01 w/w %.

Likewise, Iodixanol is the non-proprietary name of the chemical drug substance 1,3-bis(acetamido)-N,N'-bis[3,5-bis(2,3-dihydroxypropylaminocarbonyl)-2,4,6-triiodophenyl]-2-hydroxypropane). The drug product is marketed under the trade name Visipaque®. The final step of the iodixanol primary production is the dimerisation of the intermediate 5-acetamido-N,N'-bis(2,3-dihydroxypropyl)-2,4,6-triiodoisophthalamide (Compound A). Reference is made to U.S. Pat. No. 6,974,882. The reaction mixture, or composition, after the dimerisation of Compound A to iodixanol also includes a considerable amount of salts, mainly in the form of sodium chloride (NaCl), as an impurity. The crude composition may comprise as much as up to 20 w/w % NaCl content relative to iodixanol, such as 10-15 w/w % relative to iodixanol, before the purification. The sources of chloride are epichlorohydrin and hydrochloric acid, which is used to adjust the pH before epichlorohydrin addition and to precipitate unreacted Compound A after the reaction. The source of sodium cations is the sodium hydroxide (NaOH) used to dissolve Compound A in the reaction solvent. Iodixanol has to be purified by desalinating the composition before crystallization. In order to crystallize iodixanol in accordance with the regulatory purity requirement, the salt content prior to the crystallization process should be less than about 0.7 w/w % relative to iodixanol.

It is thus desirable to devise a cost effective procedure for desalinating compositions comprising a contrast agent, such as prepared in the primary production.

To achieve such low salt levels in the composition comprising the contrast agent as required for iohexol and iodixanol, many attempts have been made to devise a process to effectively and efficiently reduce large salt contents generated in primary production. Such known methods include various techniques involving filtration, such as nano-filtration and ultra-filtration, use of purification columns, ion exchange and dialysis.

U.S. Pat. No. 5,210,300 by Mallinckrodt is directed to a method of purifying the X-ray contrast agent ioversol by removing acids and other impurities by continuous deionization. Crude ioversol is passed through a mixed-bed resin and an electrical current is applied. However, as use of traditional electrodeionization (EDI) systems are disclosed it is believed that challenges such as leakage of the contrast agent from the feed stream is experienced. Further, poor exploitation of energy is likely to be seen.

Hence, an alternative, and preferably improved process, has been sought for reducing the salt content of crude compositions comprising an X-ray contrast agent or an MR contrast agent, particularly in industrial scale.

Thus, in a first aspect the invention provides a process for the preparation of a composition comprising a contrast agent in a carrier, the process comprising the step of desalinating the composition by electrodeionization using a wafer based EDI device.

Electrodeionization (EDI), also called electrochemical deionization, is a process that removes ionizable species from liquids using an ionically active media and an electrical potential to influence ionic transport. EDI devices combine the use of ion exchange resins, ion exchange membranes and electrodes without the need for regeneration of chemicals. The EDI cell combines the benefits of ion exchange and electrodialysis while minimizing the problems associated with each of these separate technologies. The EDI cell uses the ion exchange resin to provide high ionic conductivity to the normally high resistance found in the dilute compartments of an electrodialysis cell. The resin's high ionic capacity increases the residence time of the ionic contaminants inside the cell allowing more time for the transport of these ions into the appropriate compartments. The electrodes generate a potential gradient for ionic movement within the cell. At cation/anion (resin/resin and resin/membrane) interfaces water is dissociated into its constituent ions, H+ and OH−, which regenerate the resins on-line, so there is no down time or need for regenerative chemicals as in ion exchange. Processes using electrodeionization to remove ions have been known from the mid-1950s, and EDI has mainly been used in the production of pure or ultrapure water for industrial processes. Applications have included pharmaceuticals and particularly production of pure feed water for pharmaceuticals and food and beverage applications, high quality rinsing water for electronics, and use in laboratories. EDI has normally not been used in chemical processing because it leaked and used electricity inefficiently. We have now surprisingly found the EDI may be beneficially used in the preparation of compositions comprising contrast agents to desalinate such by using a wafer based EDI device. Such EDI devices provide an improved electrical flow over other EDI systems and have a less tendency to leak the product which is to be purified.

The EDI device used in the process of the invention comprises an ion exchange resin, membranes and means for applying a DC voltage, wherein the ion exchange resin is moulded into a porous wafer. In one embodiment the ion exchange resin comprises wafers of uniform thickness. Different types of ion exchange resins may be used in the same system. The ion exchange resin consists of a porous ion-exchange material or is alternatively in gel form. U.S. Pat. No. 6,495,014 discloses relevant wafer-based EDI devices and the subject matter of this patent, particularly regarding the EDI device, is hereby incorporated by reference.

In a particularly preferred embodiment the EDI device used in the process of the invention comprises
a cation-exchange membrane;
an anion-exchange membrane, preferably juxtaposed coplanarly to said cation exchange membrane;
a porous ion-exchange resin material, preferably positioned intermediate said cation-exchange membrane and said anion exchange membrane to form a compartment, preferably whereby the material comprises anion-exchange entities and cation exchange entities immobilized relative to each other via a binder which comprises said material, preferably with at least 20 weight percent;
and a means for applying an electrical potential to said compartment, wherein the entities are preferably embedded in a thermoplastic, such as selected from the group consisting of low linear density polyethylene, high density polyethylene, and combinations thereof.

The electrodeionization process of the invention can be batch wise or continuous. The continuous electrodeionization (CEDI) process of the invention employs anion and cation permeable ion exchange membranes, with the porous ion exchange resins packed between them. The typical process includes separate diluting and concentrating compartments. Applying a DC electric potential causes ions to move from one compartment to another, affecting a separation. Since the concentration of ions is reduced in one compartment and increased in the other, the process can be used for either purification or concentration. Under the influence of the electric field, cations will migrate in the direction of the negatively charged cathode, through the cation-exchange resin, cation-permeable membrane and into the concentrating stream. An anion permeable membrane on the opposite side of that stream prevents further migration, effectively trapping the cations in the concentrating stream. The process for anion removal is analogous, but in the opposite direction, toward the positively charged anode. Most commercially available CEDI modules are plate and frame devices with multiple arrangements of alternating diluting and concentrating compartments, hydraulically in parallel and electrically in series, and such CEDI devices may be used in the process of the invention.

The process of the invention addresses the specific need of the current iohexol and iodixanol synthesis methodology, wherein large amounts of salts are generated as a result of the alkylation or dimerisation steps, and wherein the requirements to purity is high. Particularly, for iohexol the salt content of the crude composition, before the crystallization step, must be very low, and the process of the invention addresses this requirement. The process further applies to similar contrast agents and compositions prepared by processes generating salts. The instant process represents a significant improvement over the alternative of employing ion exchange resins. For example, two ion exchange resins, one anionic and one cationic, are needed to remove the significant amount of salts present following the alkylating reaction when preparing iohexol. The requirement of two resins, both in large quantities, causes significant loss of intermediates and final product, such as of Compound A and iohexol for the iohexol process.

With the process of the invention a low leakage and a low energy consumption is seen. Hence, one improvement of the instant process is that the loss of the main product, i.e. the contrast agents such as iohexol or iodixanol, is kept at a minimal during electrodeionization. In addition, the operation of large scale purifications using ion exchange resins includes separation time, energy consumption, cost of resin regeneration and replacement, i.e. an equipment requirement which is lengthy, complex, and expensive. With the wafer based EDI device the energy consumption is lower and costs are reduced. Another advantage of the wafer used in the present invention is that a section or cell comprising ion exchange resins can easily be lifted out. With the process of the invention there is no need to use chemicals such as hydrogen chloride and sodium hydroxide in the regeneration of the ion exchange resins. Less water is further likely to be needed, and this will result in less water needed to be removed and less strains of the contrast agent.

The term "contrast agents" denotes agents that comprise a material that can significantly attenuate incident radiation causing a reduction of the radiation transmitted through the volume of interest. Increased radiation attenuation is interpreted as an increase in the density of the volume of interest, which creates a contrast enhancement in the volume comprising the contrast agent relative to the background tissue in the image. Preferably, contrast agent denotes an X-ray contrast agent or a magnetic resonance imaging (MRI) contrast agent, and most preferably an X-ray contrast agent. The X-ray contrast agent of the composition prepared by the process of the invention can be any type of X-ray agent. The process of the invention is hence useful for compositions comprising any X-ray agent and further comprising salts that should be removed from the composition. The primary production of X-ray agents typically includes a multi step chemical synthesis. For such agents there are alternative synthesis schemes and the synthesis also depend on the agents to produce. However, in such synthesis there are some similarities, e.g. in that different reagents, acids and bases are used which may form salts that have to be removed from the composition, e.g. before crystallization of the agent and/or after crystallization has taken place.

The contrast agent of the produced composition is preferably an iodinated X-ray compound. Preferably this is a non-ionic iodinated monomeric compound or a non-ionic iodinated dimeric compound, i.e. a compound comprising single triiodinated phenyl groups or a compound comprising two linked triiodinated phenyl groups. However, trimeric, tetrameric and pentameric compounds are also included. Relevant monomeric and dimeric compounds are provided by the applicant's application EP2010/050118. Particularly relevant contrast agents that are monomeric compounds are described in WO97/00240 and in particular the compound BP257 of example 2, and additionally the commercially available compounds iohexol, iopamidol, iomeprol, ioversol, iopromide, iobitridol and iopentol. Most particularly preferred are the compounds iohexol and iopamidol. In one embodiment, ioversol is disclaimed from the process of the invention.

Particularly relevant contrast agents that are dimeric compounds are iodixanol (Visipaque) and compounds described in WO2009/008734, and particularly the compound of formula (I), now called Ioforminol, agents are chelators selected from the group of DTPA, DTPA-BMA, DOTA, HPDO3A, preferably chelating a metal selected from the group of gadolinium (Gd), praseodymium (Pr), dysprosium (Dy), europium (Eu), thulium (Tm) and manganese (Mn). Particularly preferred is the contrast agent GdDTPA-BMA which is a low molecular weight paramagnetic contrast agent used in magnetic resonance imaging (MRI), known as Omniscan®. In the preparation of such contrast agents, both in the synthesis of the chelator and in the preparation of the metal chelate, salts are generated, and such salts should be removed from the generated composition. In the preparation of GdDTPA-BMA methyl amine is used as a reagent in preparation of the chelator and HCl is used for pH adjustment. Before addition of the gadolinium, salts like methylamine hydrochloride should be removed. Other salts, like NaCl may also be removed by the EDI process. Further, after complexing with a metal, free metal ions, like $Gd^{3+}$, may also be removed by the process of the invention.

For the embodiment wherein the contrast agent is an X-ray contrast agent, such as iohexol or iodixanol, the process of the invention is either carried out before crystallization of the contrast agent and/or after such crystallization. Preferably, the process of using EDI for desalination of the contrast agent is carried out before crystallization.

However, in addition, or instead, the process of the invention, desalinating a composition comprising a contrast agent, can be used after crystallization for a further bulk treatment, or so called "polishing step", to further purify the contrast agent before drying. Such polishing step includes dissolving the filtered crystallized contrast agent in water and desalinating such composition by the EDI process of the invention. Generally speaking, a process of the invention can include additional desalinating by electrodialysis (ED) in a separate step before or after the EDI step.

In a particularly preferred embodiment, the invention provides a process for the preparation of an X-ray compo- Formula (I)

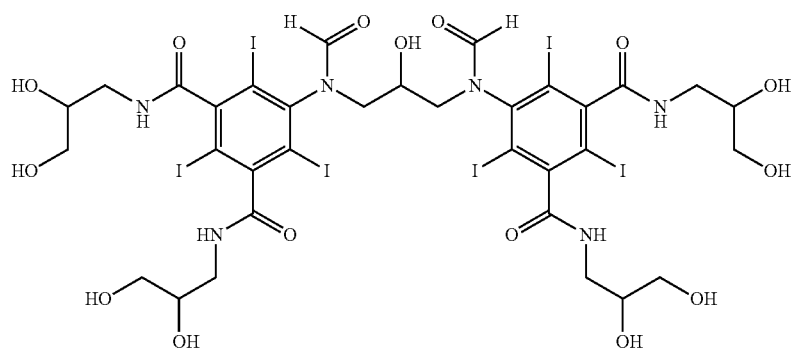

The patent applications referred to, i.e. particularly EP2010/050118 and WO2009/008734, are hereby incorporated by reference.

In one embodiment of the invention, the contrast agent of the composition to be desalinated is an MRI contrast agent. Preferred contrast generating species in MR imaging spectroscopy are paramagnetic compounds such as stable free radicals, compounds comprising transition metals and compounds comprising lanthanide metals. Such contrast agents are preferably transition metal chelates, transition metal salts and lanthanide metal chelates, e.g. manganese salts, gadolinium chelates or dysprosium chelates. Preferred contrast sition comprising the contrast agent iohexol, the process comprising the step of desalinating a crude composition comprising iohexol by electrodeionization using a wafer based EDI device, including the sequential steps of:
(1) reducing the salt content in a crude composition which is the reaction mixture comprising Compound A, salts and iohexol, by EDI;
(2) crystallizing iohexol from the composition of step (1).

In another preferred embodiment, the invention provides a process for the preparation of an X-ray composition comprising the contrast agent iodixanol, the process comprising the step of desalinating a crude composition comprising iodixanol by electrodeionization using a wafer based EDI device, including the sequential steps of:

(1) reducing the salt content in a crude composition which is the reaction mixture comprising Compound A, salts and iodixanol, by EDI;

(2) recovering Compound A in the composition of (1) after desalination, for reuse in a subsequent dimerisation reaction to prepare iodixanol; and (3) crystallizing iodixanol from the composition of step (1).

Compound A is 5-acetamido-N,N'-bis(2,3-dihydroxypropyl)-2,4,6-triiodoisophthalamide.

For the process above for iodixanol, the side stream from step (2) comprising feeding unreacted reagent Compound A back for another dimerisation reaction could also be subjected to desalinating by the process of the invention.

The crystallized contrast agent, such as iohexol or iodixanol, may be subjected to the additional bulk treatment steps of:

a) dissolving the crystallized contrast agent in water
b) purifying the composition from step (a),
c) drying the composition from step (b).

The purification of the composition from step a) includes further desalination of the contrast agent and removal of other impurities, and may include the use of ion exchange treatment, treatment with charcoal, and/or desalination by EDI, preferably using a wafer based EDI device, according to the process of the invention.

In yet another embodiment of the invention, the composition comprising a contrast agent subjected to the desalinating process is a side stream or waste stream from the process of preparing a contrast agent, and this composition typically comprises minor amounts of the contrast agent, such as less than 10%, even less than 1%. By desalinating and purifying such side stream or waste stream this can go to proper waste disposal. By separating out e.g. salts from remains of the main product (contrast agent), intermediates or byproducts, these can be sent to recycling of e.g. iodine.

By using the process of the invention the salt content of the composition after the process has been conducted, is less than about 1.0%, more preferably less than 0.7 weight %, or even less than 0.6 weight %, compared to the contrast agent content. In a preferred embodiment, the salt content in the composition comprising iodixanol is less than about 0.7 weight %, or even less than 0.6 weight %, compared to the iodixanol content. In another preferred embodiment, the salt content in the composition comprising iohexol is less than about 0.02 weight %, or even 0.01% or less, compared to the iohexol content.

The salts generated in the preparation of iohexol and iodixanol are mainly NaCl, but other salts such as acetates and formates, e.g. in the form of sodium acetates and formates, could equally be removed according to the process of the invention.

The desalination process of the invention, conducted either before or after crystallization of the contrast agent, may be combined with other methods for removing salts or other impurities. Such other methods are preferably selected from filtrations, ion exchange and electrodialysis. In a preferred embodiment the process comprises the step of desalinating the composition by electrodeionization (EDI), combined with an additional desalinating by electrodialysis (ED) in a separate step before the EDI step. In such preferred embodiment, a composition comprising a contrast agent and salts to be removed, is subjected to ED first to remove the majority of the salts, followed by a step of subjecting the composition to EDI to further lower the salt content, removing the last remaining salts which are difficult to remove by other methods. The electrodeionization is preferably conducted using a wafer based EDI device.

In yet another embodiment, the process of the invention comprising the step of desalinating an X-ray composition by electrodeionization, is included in a continuous process for preparing an X-ray contrast agent. In a batch process, all the operations are performed successively in the same reactor. Thus, production capacity increase in a batch production requires very large reactor volumes and a corresponding increase in capital investments. On the other hand, a continuous process has dedicated equipment for every operation, where the mixture moves from one operation to the next within the production line. All the operations are performed continuously all the time and the system is at a steady state. Consequently, a continuous production process requires much smaller equipment volumes and investments for achieving the same production capacity. In addition, a continuous operation allows for less varying quality of the product. While desirable, a continuous system is more complicated to design and highly specific to one single product. We have however found that the synthesis of the contrast agent, and the subsequent desalination of the composition comprising the contrast agent, can be performed in a continuous mode. The contrast agent is preferably an iodinated X-ray compound and the primary production of such would hence include a multi step chemical synthesis including e.g. iodination and alkylation and/or dimerisation step, followed by the desalination process of the invention, performed in a continuous mode. Alternatively, the contrast agent is an MM contrast agent. In one embodiment, some steps of the process for preparing a contrast agent are batch wise, while other are included in a continuous mode. In another embodiment, such continuous process includes the process of the invention, i.e. desalinating the crude composition comprising the contrast agent, and in addition including some or all of the following steps necessary to purify the contrast agent before secondary production. Such following steps e.g. include filtration of the contrast agent after crystallization, solving this in water, purifying by e.g. ion exchange, treatment with charcoal, ED and/or EDI, and evaporation, to obtain a pure contrast agent. The instant continuous process gives significant benefits in reduced cycle times, reduced amount of equipment required in a production line, reduced headcount and a stabilized process with resulting consistent product quality in terms of yield, impurity profile and physical characteristics of the product.

The invention is illustrated further by the following examples that are not to be construed as limiting the invention in scope to the specific procedures described in them.

EXAMPLES

Example 1

Preparation and Purification of Iodixanol

5-Acetamido-N,N'-bis(2,3-dihydroxypropyl)-2,4,6-triiodoisophthalamide (Compound A) (600 kg) is reacted with epichlorohydrin (0.33 eq) in an alcoholic solvent in the presence of sodium hydroxide at a pH of about 11.9 at 15° C. About 55% conversion to iodixanol is obtained. Most of unreacted Compound A is precipitated from the reaction mixture by addition of hydrochloric acid followed by filtration. The aqueous filtrate contains about 340 kg iodixanol, 100 kg Compound A and 20 kg iohexol. The pH is measured to about 4-6. The NaCl content is about 12-14 w/w % relative to iodixanol. The solution is then subjected to a membrane filtration or an electro dialysis followed by electrodeionization using a wafer based EDI, for salt removal and for separating out Compound A, resulting in an aqueous process solution ready for the next process including the crystallization step.

Example 2

Preparation and Purification of Iohexol

After alkylation of "Compound A" with 3-chloro-1,2-propanediol in an alcoholic solvent in the presence of sodium hydroxide, and termination of the reaction with hydrochloric acid, the following crude reaction mixture is obtained: An about 40 w/v solution of iohexol (about 99 area % purity by HPLC) in an alcoholic solvent containing about 3 w/w % NaCl (3 g NaCl/100 g iohexol) and traces of unreacted 3-chloro-1,2-propanediol and traces of sodium acetate. The solution is then subjected to ED followed by wafer based EDI, resulting in an aqueous process solution ready for the next process including the crystallization step.

Example 3

Bulk Treatment of Crystallized Iohexol

After crystallization of iohexol, the crystallized product is solved in water (ca. 40 w/v % iohexol). The last remaining salt is removed in this bulk treatment step (polishing step). To obtain a salt content of 0.01 w/w %, or lower compared to iohexol content, the solution is subjected to wafer based EDI. After this bulk treatment the composition is subjected to bulk concentrating and drying.

Example 4

DTPA-BMA Synthesis and Purification

DTPA bis(anhydride) is reacted with an excess methyl amine (3 equivalents) to prepare DTPA-BMA and the pH is adjusted to about pH 3. Before complexing the chelator with gadolinium, the obtained solution is subjected to electrodeionization by using a wafer based EDI for removal of methylamine hydrochloride.

I claim:

1. A process for purifying a first composition comprising (i) a contrast agent selected from the group consisting of iohexol, iodixanol, ioforminol, and a magnetic resonance (MR) contrast agent, and (ii) at least one salt, the process comprising:
    desalinating the first composition by electrodeionization (EDI), using a wafer-based EDI device, to yield a second composition including the contrast agent and a first reduced concentration of the at least one salt;
    performing one of purifying and desalinating the second composition using electrodialysis (ED) to yield a third composition including the contrast agent and a second reduced concentration of the at least one salt;
    crystallizing the third composition to yield a crystallized third composition including a crystallized contrast agent and the at least one salt;
    dissolving the crystallized third composition in a solvent to yield a fourth composition; and
    purifying the fourth composition to further reduce a concentration of the at least one salt in the fourth composition.

2. The process of claim 1, wherein the contrast agent is the magnetic resonance (MR) contrast agent.

3. The process of claim 1, wherein the first composition further includes 5-acetamido-N, N'-bis(2,3,dihydroxypropyl)-2,4,6-triiodoisophtalamide (Compound A).

4. The process of claim 1, wherein purifying the fourth composition includes desalinating the fourth composition using EDI.

5. The process of claim 4, wherein desalinating the fourth composition includes using another wafer-based EDI device.

6. The process of claim 1, wherein when the contrast agent is iodixanol, the concentration of the at least one salt in the fourth composition is less than about 0.7 weight % relative to the iodixanol content in the fourth composition, after the process has been conducted.

7. The process of claim 1, wherein the wafer-based EDI device includes ion exchange resins and membranes, and wherein the ion exchange resins are molded into a porous wafer.

8. The process of claim 3, further comprising, when the contrast agent is iodixanol, recovering Compound A after desalinating the first composition.

9. The process of claim 8, wherein the concentration of the at least one salt in the fourth composition is less than about 1.0% relative to the iodixanol content in the fourth composition, after the process has been conducted.

10. The process of claim 4, wherein the concentration of the at least one salt in the fourth composition is less than about 1.0% relative to the contrast agent content in the fourth composition, after the process has been conducted.

11. The process of claim 1, further comprising drying the fourth composition after purifying the fourth composition.

12. The process of claim 1, wherein, when the contrast agent is iohexol, the concentration of the at least one salt in the fourth composition is less than about 0.02 weight % relative to the iohexol content in the fourth composition, after the process has been conducted.

13. The process of claim 12, wherein purifying the fourth composition includes reducing the concentration of the at least one salt below a specified threshold.

14. The process of claim 12, wherein the concentration of the at least one salt in the fourth composition is less than about 0.01 weight % relative to the iohexol content in the fourth composition, after the process has been conducted.

15. The process of claim 1, wherein, after the process has been conducted, the concentration of at least one salt in the fourth composition is selected from the group consisting of (i) less than about 1.0% relative to the contrast agent content in the fourth composition, (ii) less than about 0.7 weight % relative to the contrast agent content in the fourth composition, and (iii) less than about 0.6 weight % relative to the contrast agent in the fourth composition.

16. The process of claim 1, wherein the process is a continuous process.

17. The process of claim 1, wherein the process is a combination of a continuous process and a batch process.

* * * * *